US009778205B2

(12) United States Patent
Hess et al.

(10) Patent No.: US 9,778,205 B2
(45) Date of Patent: Oct. 3, 2017

(54) DELTA DIE AND DELTA DATABASE INSPECTION

(71) Applicant: KLA-Tencor Corporation, Milpitas, CA (US)

(72) Inventors: Carl E. Hess, Los Altos, CA (US); Yanwei Liu, Danville, CA (US); Yalin Xiong, Union City, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 243 days.

(21) Appl. No.: 14/664,565

(22) Filed: Mar. 20, 2015

(65) Prior Publication Data

US 2015/0276617 A1     Oct. 1, 2015

Related U.S. Application Data

(60) Provisional application No. 61/969,984, filed on Mar. 25, 2014, provisional application No. 61/969,990, filed on Mar. 25, 2014.

(51) Int. Cl.
*G06K 9/00*     (2006.01)
*G01J 1/46*     (2006.01)
(Continued)

(52) U.S. Cl.
CPC ... *G01N 21/8851* (2013.01); *G01N 21/95607* (2013.01); *G03F 1/84* (2013.01); *G01N 2021/95676* (2013.01)

(58) Field of Classification Search
CPC .... G01N 2021/95615; G01N 21/95607; G06T 2207/10056; G06T 2207/20021; G06T 2207/30148; G06T 7/001
(Continued)

(56) References Cited

U.S. PATENT DOCUMENTS 6,614,520 B1    9/2003   Bareket et al.
7,069,155 B1    6/2006   Phan et al.
(Continued)

FOREIGN PATENT DOCUMENTS

CN     101295130 A    10/2008
JP      06174652 A     6/1994
(Continued)

OTHER PUBLICATIONS

"U.S. Appl. No. 13/757,103, Final Office Action mailed Jul. 14, 2016", 35 pgs.
(Continued)

*Primary Examiner* — Sheela C Chawan
(74) *Attorney, Agent, or Firm* — Kwan & Olynick LLP

(57) ABSTRACT

Disclosed are methods and apparatus for inspecting a photolithographic reticle. An inspection tool is used to obtain a plurality of patch area images of each patch area of each die of a set of identical dies on a reticle. An integrated intensity value for each patch area image is determined. A gain is applied to the integrated intensity value for each patch area image based on a pattern sparseness metric of such patch area image and its relative value to other patch area images' pattern sparseness metric. A difference between the integrated intensity value of each patch of pairs of the dies, which each pair includes a test die and a reference die, is determined to form a difference intensity map of the reticle. The difference intensity map correlates with a feature characteristic variation that depends on feature edges of the reticle.

27 Claims, 10 Drawing Sheets

(51) Int. Cl.
*G01N 21/88* (2006.01)
*G01N 21/956* (2006.01)
*G03F 1/84* (2012.01)

(58) Field of Classification Search
USPC .............. 382/100, 141, 144, 145, 149, 151; 348/126, 125, 129; 356/215
See application file for complete search history.

(56) References Cited

U.S. PATENT DOCUMENTS

| | | | |
|---|---|---|---|
| 7,564,545 B2 | 7/2009 | Stokowski | |
| 7,853,920 B2* | 12/2010 | Preil | G03F 1/84 |
| | | | 382/149 |
| 8,421,026 B2* | 4/2013 | Ben-Zvi | G03F 1/84 |
| | | | 250/372 |
| 8,855,400 B2 | 10/2014 | Wang et al. | |
| 2002/0085297 A1 | 7/2002 | Boettiger et al. | |
| 2004/0240723 A1 | 12/2004 | Sakai et al. | |
| 2005/0004774 A1 | 1/2005 | Volk et al. | |
| 2005/0166171 A1 | 7/2005 | Bartov | |
| 2005/0174570 A1 | 8/2005 | Kvamme et al. | |
| 2006/0038987 A1 | 2/2006 | Maeda et al. | |
| 2008/0052021 A1 | 2/2008 | Morinaga et al. | |
| 2008/0170773 A1 | 7/2008 | Wihl et al. | |
| 2008/0304056 A1 | 12/2008 | Alles et al. | |
| 2009/0037134 A1 | 2/2009 | Kulkarni et al. | |
| 2009/0136116 A1 | 5/2009 | Okai et al. | |
| 2009/0226076 A1 | 9/2009 | Sakai et al. | |
| 2012/0002860 A1 | 1/2012 | Sakai et al. | |
| 2013/0211736 A1* | 8/2013 | Hess | G03F 1/84 |
| | | | 702/34 |
| 2014/0168418 A1 | 6/2014 | Hess | |

FOREIGN PATENT DOCUMENTS

| | | |
|---|---|---|
| JP | 2004271421 A | 9/2004 |
| JP | 2006018054 A | 1/2006 |
| JP | 2006080437 A | 3/2006 |
| KR | 1020100069503 A | 6/2010 |
| WO | 2011035946 A1 | 3/2011 |
| WO | 2012012265 A2 | 1/2012 |
| WO | 2013142079 A1 | 9/2013 |

OTHER PUBLICATIONS

"Chinese Application Senal No. 201380018790.X, Office Action mailed Mar. 29, 2016", 19 pgs.
"International Application Serial No. PCT/US2015/022340, Search Report", 2 pgs.
"International Application Serial No. PCT/US2013/026224, Search Report and Written Opinion mailed Jun. 3, 2013", 11 pgs.
"International Application Serial No. PCT/US2013/074841, Search Report and Written Opinion mailed Sep. 25, 2014", 12 pgs.
"Int'l Application Serial No. PCT/US2013/029587, Preliminary Report on Patentability mailed Oct. 2, 2014", 8 pgs.
"Int'l Application Serial No. PCT/US2013/029587, Search Report and Written Opinion mailed Jun. 24, 2013", 3 pgs.
Sagiv, Amir et al., "IntenCD: Mask Critical Dimension Variation Mapping", Proc. of SPIE vol. 7028, 70282X, Retrieved from the Internet: < http://proceedings.spiedigitallibrary.org/ on Jan. 14, 2013 Terms of Use: http://spiedl.org/terms >, Accessed on Jan. 14, 2013, 2008, 12 pgs.

* cited by examiner

DELTA DIE AND DELTA DATABASE INSPECTION

CROSS-REFERENCE TO RELATED APPLICATIONS

This application claims priority under 35 U.S.C. §119 of prior U.S. Provisional Application No. 61/969,984, filed 25 Mar. 2014, titled "Delta Die Enhancements" by Carl E. Hess et al. and U.S. Provisional Application No. 61/969,990, filed 25 Mar. 2014, titled "Delta Database Critical Dimension Uniform Map" by Carl E. Hess et al., which applications are herein incorporated by reference in their entirety for all purposes.

TECHNICAL FIELD OF THE INVENTION

The invention generally relates to the field of semiconductor inspection, such as reticle inspection. More particularly the present invention relates to a method to monitor critical dimension uniformity and the like.

BACKGROUND

Generally, the industry of semiconductor manufacturing involves highly complex techniques for fabricating integrating circuits using semiconductor materials which are layered and patterned onto a substrate, such as silicon. An integrated circuit is typically fabricated from a plurality of reticles. Initially, circuit designers provide circuit pattern data or a design database, which describes a particular integrated circuit (IC) design, to a reticle production system, or reticle writer. The circuit pattern data is typically in the form of a representational layout of the physical layers of the fabricated IC device. The representational layout includes a representational layer for each physical layer of the IC device (e.g., gate oxide, polysilicon, metallization, etc.), wherein each representational layer is composed of a plurality of polygons that define a layer's patterning of the particular IC device. The reticle writer uses the circuit pattern data to write (e.g., typically, an electron beam writer or laser scanner is used to expose a reticle pattern) a plurality of reticles that will later be used to fabricate the particular IC design.

Each reticle or photomask is generally an optical element containing at least transparent and opaque regions, and sometimes semi-transparent and phase shifting regions, which together define the pattern of coplanar features in an electronic device such as an integrated circuit. Reticles are used during photolithography to define specified regions of a semiconductor wafer for etching, ion implantation, or other fabrication processes.

A reticle inspection system may inspect the reticle for defects that may have occurred during the production of the reticles or after use of such reticles in photolithography. Due to the large scale of circuit integration and the decreasing size of semiconductor devices, the fabricated devices have become increasingly sensitive to defects. That is, defects which cause faults in the device are becoming smaller. Accordingly, there is a continuing need for improved inspection techniques for monitoring characteristics of the reticle.

SUMMARY

The following presents a simplified summary of the disclosure in order to provide a basic understanding of certain embodiments of the invention. This summary is not an extensive overview of the disclosure and it does not identify key/critical elements of the invention or delineate the scope of the invention. Its sole purpose is to present some concepts disclosed herein in a simplified form as a prelude to the more detailed description that is presented later.

In one embodiment, methods and apparatus for inspecting a photolithographic reticle are disclosed. An inspection tool is used to obtain a plurality of patch area images of each patch area of each die of a set of identical dies on a reticle. An integrated intensity value for each patch area image is determined. A gain is applied to the integrated intensity value for each patch area image based on a pattern sparseness metric of such patch area image and its relative value to other patch area images' pattern sparseness metric. A difference between the integrated intensity value of each patch of pairs of the dies, which each pair includes a test die and a reference die, is determined to form a difference intensity map of the reticle. The difference intensity map correlates with a feature characteristic variation that depends on feature edges of the reticle.

In a specific implementation, each die's patch area images are aligned with the patch area images of a same one of the dies. In another example, the integrated intensity value for each patch area image is an average intensity value for a plurality of subareas of the patch area image. In another embodiment, the sparseness metric of each patch area image of each die is a ratio of an average number of edge pixels of the other patch area images of the die and a local number of edge pixels of such patch area image. In a further aspect, the average and local number of edge pixels are limited to a predefined width of pixels for each feature edge.

In a specific implementation, the feature characteristic variation is a critical dimension (CD) variation. In a further aspect, the method includes using a calibration factor for each patch area of the reticle to convert the difference intensity map to a difference CD map. In a further aspect, the calibration factor for each patch area is determined from a design database having a known CD value for each patch area that was used to fabricate the reticle. In yet a further aspect, the calibration factor for each patch area is determined by (i) rendering an image for each patch area of the reticle based on one or more patterns of the design database corresponding to such patch area, (ii) for each rendered image for each patch area, determining an expected integrated intensity value, (iii) by a predefined CD change, either (a) biasing each one or more patterns corresponding to each patch area and rendering the biased one or more patterns into a biased image for such patch area or (b) biasing one or more patterns of the rendered image for each patch area to form a biased image for such patch area, (iv) for each biased image for each patch area, determining an expected integrated intensity value, (v) for each patch area, determining an integrated intensity difference between the rendered image's integrated intensity value and the biased image's integrated intensity value, and (vi) for each patch, determining the calibration factor by dividing the integrated intensity difference by the predefined CD change. In a further aspect, the calibration factor is stored for each patch area to monitor CD uniformity after using the reticle in one or more photolithography processes.

In another embodiment, the method includes, for each patch area image, changing an intensity value to a predefined constant value for any flat field area of the patch area image that is positioned a predefined distance from any feature edge prior to determining the integrated intensity value. In a further aspect, the predefined distance is selected so that a feature edge does not affect a measured intensity value from an adjacent flat field area. In another embodiment, the gain that is applied to the integrated intensity value of each patch area image is limited by a predefined amount.

In an alternative embodiment, the invention pertains to an inspection system for inspecting a photolithographic reticle, and the system includes at least one memory and at least one processor that are configured to perform one or more of the above described operations. In other embodiments, the invention pertains to computer readable media having instructions stored thereon for performing at least some of the above described operations.

These and other aspects of the invention are described further below with reference to the figures.

DETAILED DESCRIPTION OF EXAMPLE EMBODIMENTS

Figure 1:
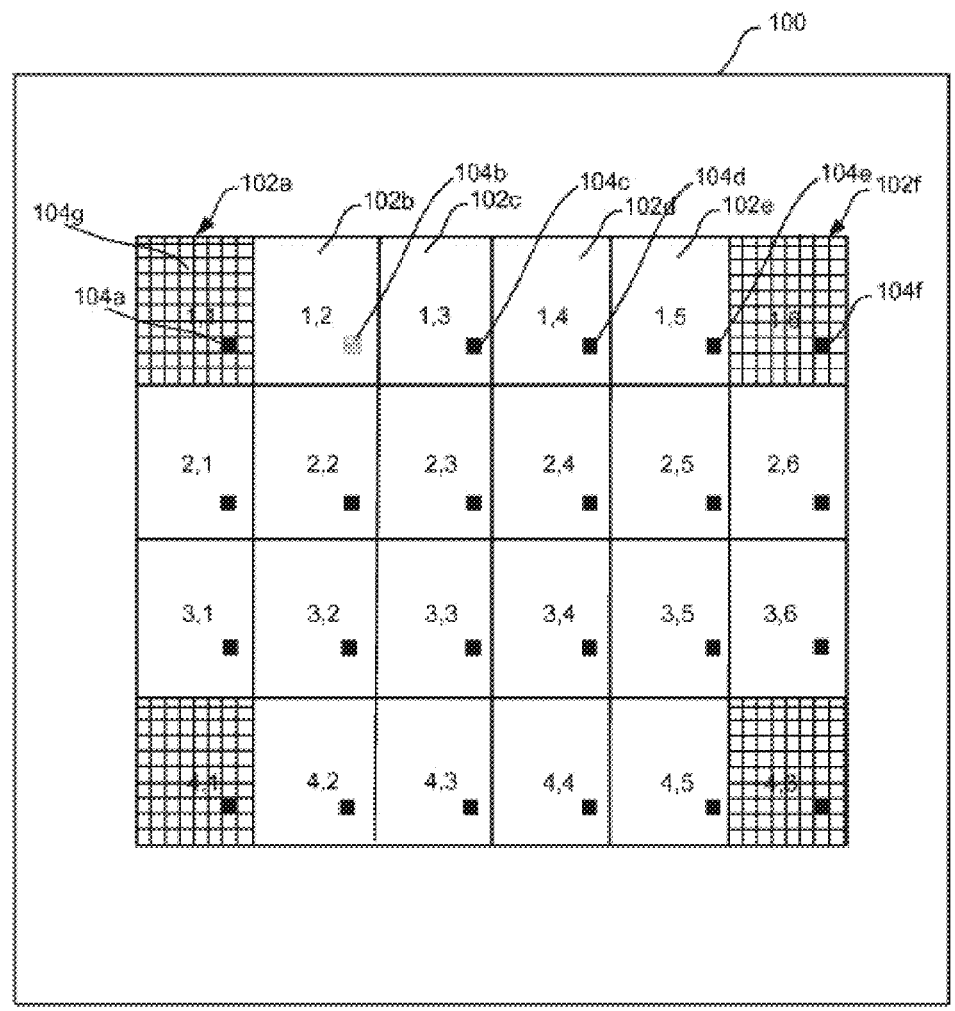
FIG. 1 is a diagrammatic top view of an example reticle having a plurality of dies.

In the following description, numerous specific details are set forth in order to provide a thorough understanding of the present invention. The present invention may be practiced without some or all of these specific details. In other instances, well known process operations have not been described in detail to not unnecessarily obscure the present invention. While the invention will be described in conjunction with the specific embodiments, it will be understood that it is not intended to limit the invention to the embodiments.

Certain embodiments of the present invention provide techniques and systems for inspecting a reticle to detect defects or, more specifically, variations in characteristics, such as critical dimension (CD), of reticle features. Although the following example embodiments are described with respect to a reticle, any suitable type of sample (e.g., wafer) may be monitored using such techniques or systems. Additionally, the following example embodiments can be applied to the monitoring of other sample characteristics, besides CD variation, such as height uniformity, sidewall angle uniformity, surface roughness uniformity pellicle transmissivity uniformity Quartz transmissivity uniformity, etc.

The terms "reticle" generally includes a transparent substrate, such as glass, borosilicate glass, quartz, or fused silica having a layer of opaque material formed thereon. The opaque (or substantially opaque) material may include any suitable material that completely or partially blocks photolithographic light (e.g., deep UV). Example materials include chrome, molybdenum silicide (MoSi), tantalum silicide, tungsten silicide, opaque MoSi on glass (OMOG), etc. A polysilicon film may also be added between the opaque layer and transparent substrate to improve adhesion. A low reflective film, such as molybdenum oxide ($MoO_2$), tungsten oxide ($WO_2$), titanium oxide ($TiO_2$), or chromium oxide ($CrO_2$) may be formed over the opaque material.

The term reticle refers to different types of reticles including, but not limited to, a clear-field reticle, a dark-field reticle, a binary reticle, a phase-shift mask (PSM), an alternating PSM, an attenuated or halftone PSM, a ternary attenuated PSM, and a chromeless phase lithography PSM. A clear-field reticle has field or background areas that are transparent, and a dark-field reticle has field or background areas that are opaque. A binary reticle is a reticle having patterned areas that are either transparent or opaque. For example, a photomask made from a transparent fused silica blank with a pattern defined by a chrome metal adsorbing film can be used. Binary reticles are different from phase-shift masks (PSM), one type of which may include films that only partially transmit light, and these reticles may be commonly referred to as halftone or embedded phase-shift masks (EPSMs). If a phase-shifting material is placed on alternating clear spaces of a reticle, the reticle is referred to as an alternating PSM, an ALT PSM, or a Levenson PSM. One type of phase-shifting material that is applied to arbitrary layout patterns is referred to as an attenuated or halftone PSM, which may be fabricated by replacing the opaque material with a partially transmissive or "halftone" film. A ternary attenuated PSM is an attenuated PSM that includes completely opaque features as well.

In general, the opaque, absorbing, partially opaque, phase-shifting material is formed into pattern structures that are designed and formed with critical dimension (CD) widths, which also results in clear spaces between the structures that also have a CD. A particular CD value may generally affect how a particular reticle feature is transferred to the wafer in the photolithography process, and such CD is chosen to optimize this transfer process. Said in another way, if a certain reticle feature's CD value is within a specified CD range, such CD value will result in fabrication of a corresponding wafer feature that allows proper operation of the resulting integrated circuit, as intended by the circuit designer. Features are typically formed with minimum dimensions that also result in operational circuits so as to conserve integrated chip area.

A newly fabricated reticle may include CD (or other film or pattern characteristic) defect issues. For example, the reticle may have defective CD regions, such as mask-writer swath-errors. A reticle may also become damaged over time in a number of different ways. In a first degradation example, the photolithographic exposure process may result in physical degradation of the opaque material of the reticle. For instance, a high power beam, such as a high powered deep ultra violet (UV) beam at 193 nm, that is used on the reticle may physically cause damage to the opaque material on the reticle. Damage may also be caused by other wavelengths, such as a 248 nm UV beam. In effect, the UV beam can physically cause the opaque patterns on the reticle to slump and causing the features to flatten. As a result, opaque features may have significantly larger CD widths, as compared to original CD widths, while the spacings between such opaque features may have a much smaller CD width, as compared with the original CD width. Other types of CD degradation may be caused by chemical reactions between the reticle features (MoSi) and the exposure light, cleaning processes, contamination, etc. These physical effects can also adversely affect the critical dimensions (CD's) of the reticle over time.

As a result of this degradation, the feature CD values may have significantly changed so as to affect CD uniformity across the reticle and adversely affect wafer yield. For instance, mask feature widths in portions of the mask may be significantly larger than the original line width CD. For instance, there may be a radial pattern of CD non-uniformity, with the center of the reticle having different CD than the edges of the reticle.

A Critical-Dimension-Uniformity (CDU) map of a reticle may be generated in order to facilitate monitoring of CD in such reticle. These CDU maps may be important for a semiconductor chip maker to understand the process window that will result from the use of the reticle. A CDU map may allow a chip maker to determine whether to use the reticle, apply compensation for the errors in the lithography process, or improve fabrication of a reticle so as to form an improved next reticle. Such CDU maps are relatively straightforward for memory masks which have repeating pattern throughout the active area, but are much more challenging for logic masks which have mostly non-repeating patterns.

A CDU map may be generated using various techniques. In a die-to-die inspection approach, the average intensity values between corresponding areas of two or more dies may be compared to obtain a delta intensity value. The delta-die values across the reticle can then effectively form a delta-intensity map, which can then be calibrated to a full CDU map. Although the following inspection techniques are described as being based on intensity type signals, other types of signals may be used in alternative embodiments of the present invention.

FIG. 1 is a diagrammatic top view of an example reticle 100 having a plurality of dies. As shown, the reticle includes a 6 by 4 array of dies that are designated by row and column. For instance, dies 102a~102f in the first top row are designated (1,1), (1,2), (1,3), (1,4), (1,5), and (1,6), from the leftmost column to the rightmost column, respectively. Similarly, the dies of the last row have designations (4,1), (4,2), (4,3), (4,4), (4,5), and (4,6) for each specific row and column.

Although the dies contain logic patterns as opposed to repeating memory patterns, the dies are designed to be identical to each other. Accordingly, each die portion (referred to as a "patch") of a particular die is expected to be identical to at least one other patch from each of the other dies. Different patches from different dies that designed to be identical are referred to herein as "die-equivalent." For instance, patch 104b of die 102b has die-equivalent patches (e.g, 104a, 104c, 104d, 104e, and 104f) in the other dies (e.g., 102a, 102c, 102d, 102e, and 102f).

During inspection, a plurality of patch images of the patches of the reticle may be obtained using an optical inspection tool. During image acquisition, multiple patch images are obtained for each die. For instance, image patches are obtained for patches 102a and 102g of die 102a. In one example die-to-die inspection approach, the image patches are obtained or defined so as to result in die-equivalent patches between the dies, and the die-equivalent patches are processed to detect CD defects or CD variation.

In a specific embodiment, an integrated intensity value for each test patch is compared to an average intensity of a reference patch (i.e., a corresponding die-equivalent patch) to obtain a delta intensity ($\Delta I$) map that can be correlated to CD variation across the reticle. The integrated intensity value of each patch may be obtained by averaging intensity values of the patch's pixels. If the reticle pattern of die-equivalent patches are identical and do not vary in CD (or any other pattern characteristic), the light from the die-equivalent patches is expected to be the same. If the intensity for a particular patch differs from the other die-equivalent reference patch, it may be inferred that the pattern of the particular patch has a CD variation as compared to the die-equivalent reference patch. For example, an increase in the transmitted intensity infers that the CD of the opaque reticle pattern has decreased and the CD of the clear reticle area has increased.

A die-to-die inspection approach works well for relatively dense patterns. However, sparse pattern regions may adversely affect the sensitivity of a die-to-die approach for monitoring a feature characteristic that pertains to a feature edge, such as CD uniformity. A sparse patch has a relatively low number of feature edges or pixels that contribute to the signal for such patch, as compared to pattern-dense patches that have a higher number of edges. Thus, a sparse patch will tend to have a lower signal corresponding to the edges than a denser patch. A low intensity signal of a low density patch may be associated with a CD change (e.g., from nominal CD), even a large CD change, and such low intensity signal may be approaching noise signal levels so that a $\Delta I$ value is not generated for such CD change. Accordingly, edge-related feature variation in sparse reticle regions may be difficult to detect.

Figure 2:
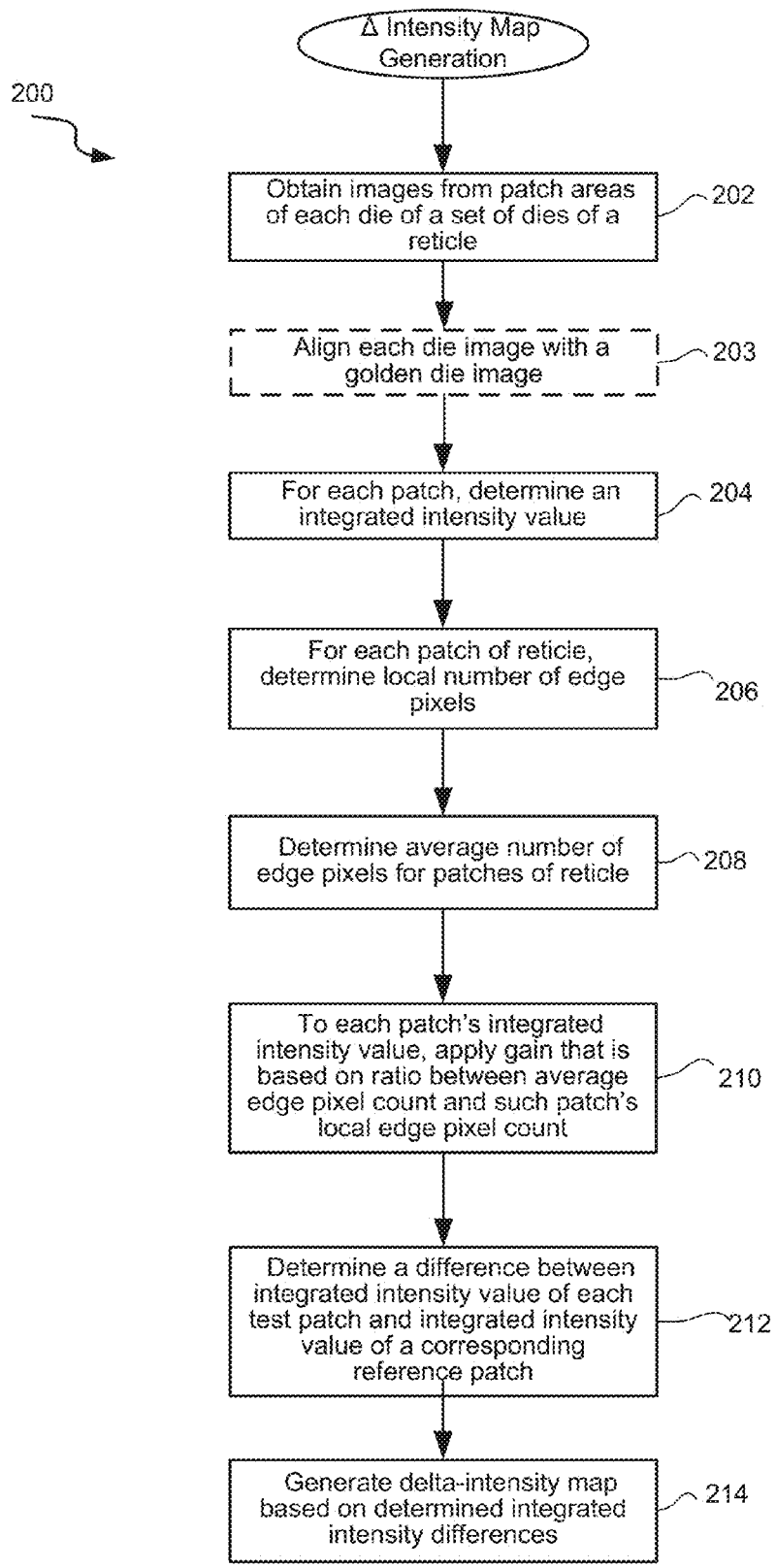
FIG. 2 is a flow chart illustrating a procedure for generating a delta-intensity map in accordance with one embodiment of the present invention.

Certain embodiments of the present invention provide techniques to bias measured intensity signals from patches based on the level of pattern sparseness for such patches. Additional techniques for reducing noise are also described herein. FIG. 2 is a flow chart illustrating a procedure 200 for generating a delta-intensity map in accordance with one embodiment of the present invention. The following inspection process 200 may be performed on a newly fabricated reticle so as to detect fabrication defective areas or performed on a reticle that has been used one or more times in a photolithography process so as to monitor features changes and/or detect degradation.

Images may be obtained from patch areas of each die of a set of dies of a reticle in operation 202. Said in another way, an inspection tool may be operable to detect and collect reflected or transmitted light or both reflected and transmitted light as an incident optical beam scans across each patch of each die of the reticle. An incident optical beam may scan across reticle swaths that each comprises a plurality of patches. Light is collected in response to this incident beam from a plurality of points or subareas of each patch.

The inspection tool may be generally operable to convert such detected light into detected signals corresponding to intensity values. The detected signals may take the form of an electromagnetic waveform having amplitude values that correspond to different intensity values at different locations of the reticle. The detected signals may also take the form of a simple list of intensity values and associated reticle point coordinates. The detected signals may also take the form of an image having different intensity values corresponding to different positions or scan points on the reticle. A reticle image may be generated after all the positions of the reticle are scanned and light is detected, or portions of a reticle image may be generated as each reticle portion is scanned.

Figure 3A:
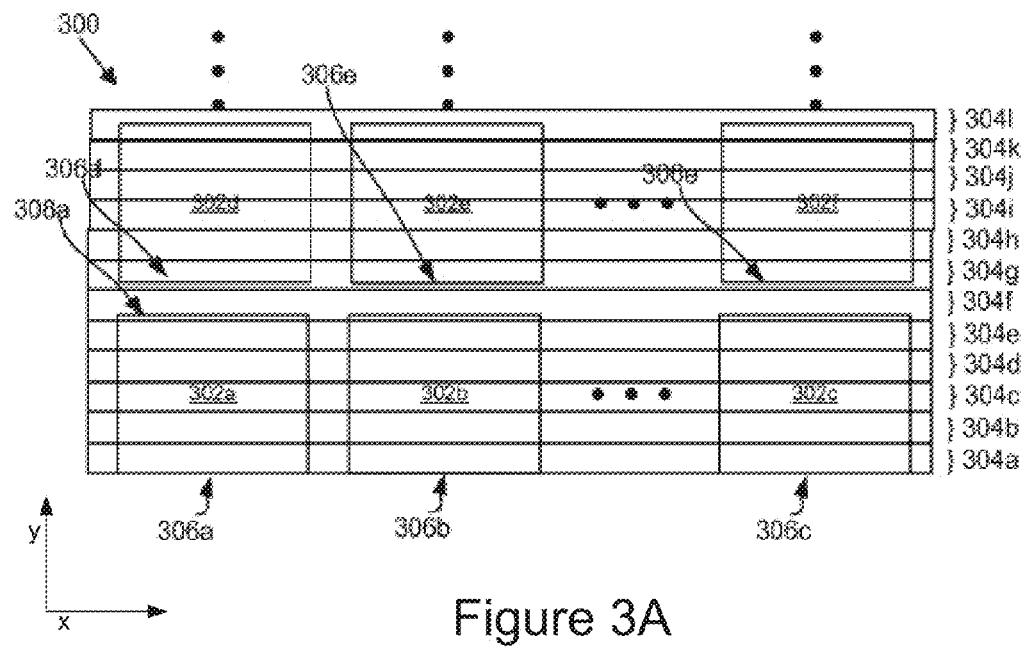
FIG. 3A is a diagrammatic representation of a plurality of scanned swaths of a reticle portion in accordance with a first implementation of the present invention.

FIG. 3A is a diagrammatic representation of a plurality of scanned/imaged "swaths" (e.g., 304a~304l) of a reticle portion 300 in accordance with embodiment of the present invention. Each set of intensity data may correspond to a "swath" of the reticle portion 300. Each set of intensity data may be obtained by sequentially scanning swaths from the reticle in a serpentine or raster pattern. For example, the first swath 304a of the reticle portion 300 is scanned by an optical beam of an optical inspection system from left to right in a positive x direction, for example, to obtain a first set of intensity data. The reticle is then moved with respect to the beam in a y direction. The second swath 304b is then scanned from right to left in a negative x direction to obtain a second set of intensity data. Swaths are sequentially scanned from the bottom row of dies through the top row of dies or visa versa.

Figure 3B:
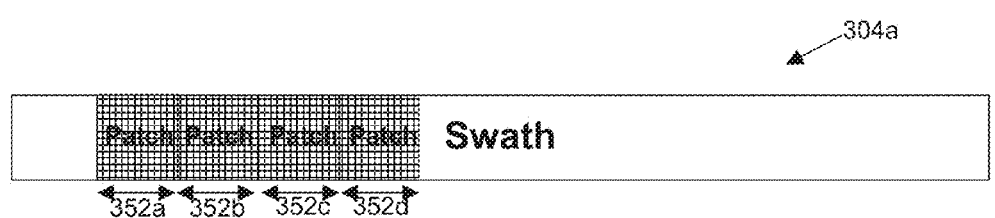
FIG. 3B is a diagrammatic illustration of an intensity data set that corresponds to a reticle swath that is divided into patches in accordance with a specific implementation.

FIG. 3B is a diagrammatic illustration of an intensity data set that corresponds to swath 304a. The intensity data for reticle swath 304a is also divided into a plurality of intensity data sets that correspond to a plurality of patches (e.g., 352a, 352b, 352c, and 352d). Although not shown, the patches tend to be overlapping to allow for eroding of the size of the effective patch image during further processing steps, for example, such as die alignment. Intensity data may be collected for multiple points in each patch of each swath.

If the scan of a swath is aligned to sweep across the same y portion with respect to the die row, each scanned swath contains die-equivalent patches from multiple dies if such dies are identical. That is, each die's patches are positioned relative to a same reference position as each of the other die's patches for which the swath is obtained. As shown, the swath 304a and its patches are positioned with respect to a bottom edge of each patch's respective die (e.g., bottom edges 306a~306c of dies 302a~302c, respectively). However, the scanned swaths of the second row of dies do not have equivalent patches with the respect to the first row of dies. In one implementation, die-equivalent patches of only a single swath may be processed together, or certain portions of the swaths and patches of the different die rows may be selected for processing so as to achieve die-equivalent patches for dies that are in different rows as further described below.

In a second implementation, image swaths are obtained for the different rows of dies so that the swaths for each die row are positioned in a similar manner with respect to the dies. Regardless of how the different die rows are scanned, an alignment process may be required to achieve true die-equivalent patches between test and reference die patches as further described below.

Figure 3C:
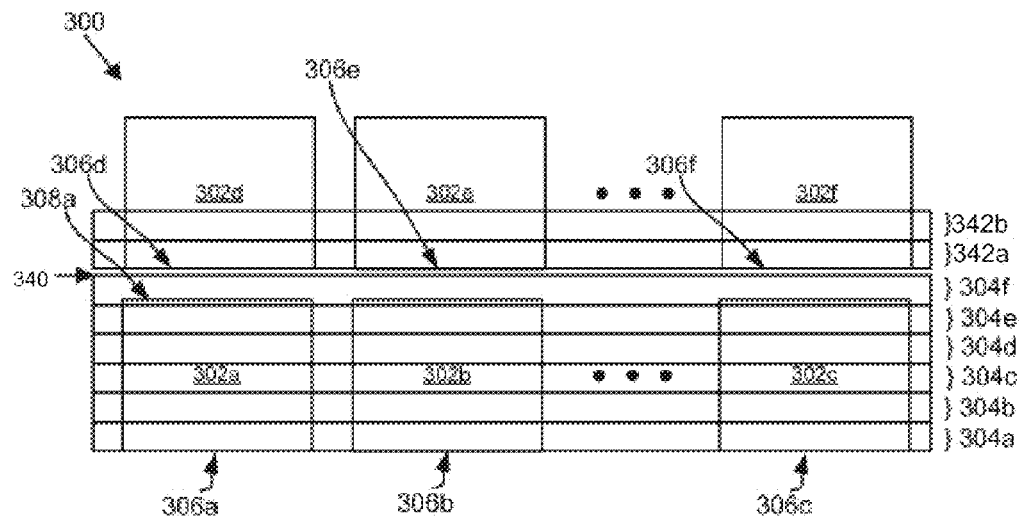
FIG. 3C illustrates a plurality of scanned swaths of a reticle in accordance with a second implementation of the present invention.

FIG. 3C illustrates a plurality of scanned swaths of a reticle in accordance with a second implementation of the present invention. As shown, the scanned swaths are positioned relative to the dies so that die-equivalent patch images may be more readily achieved across multiple swaths and multiple die rows. For example, swaths 342a and 304a are positioned in a substantially same $1^{st}$ row of their corresponding dies (e.g., 302a~302f), while swaths 342b and 304b are positioned in a substantially same $2^{nd}$ row of their corresponding dies (e.g., 302a~302f).

Figure 4:
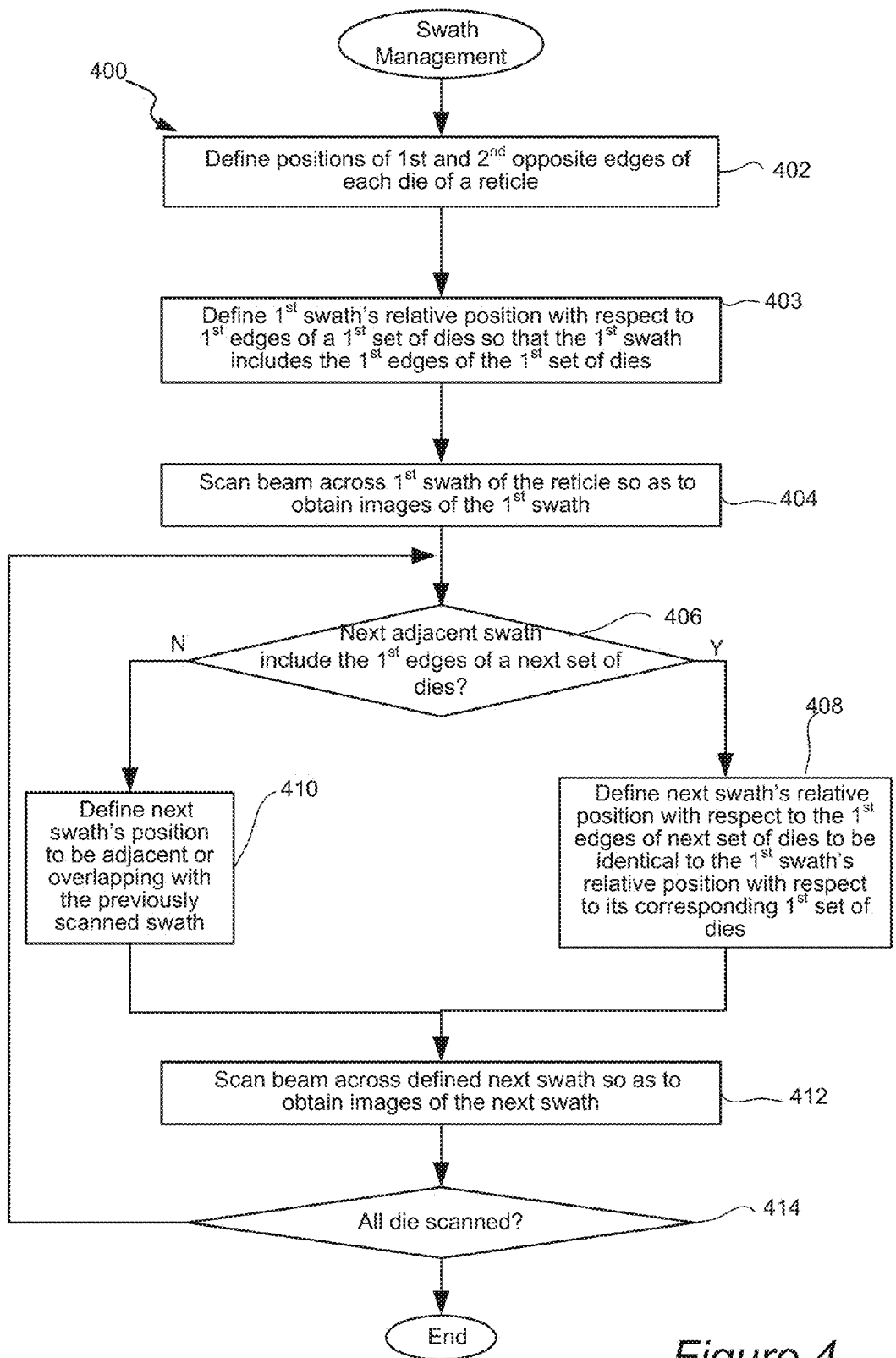
FIG. 4 is a flow chart illustrating a procedure for swath management in accordance with a second implementation of the present invention.
Figure 5:
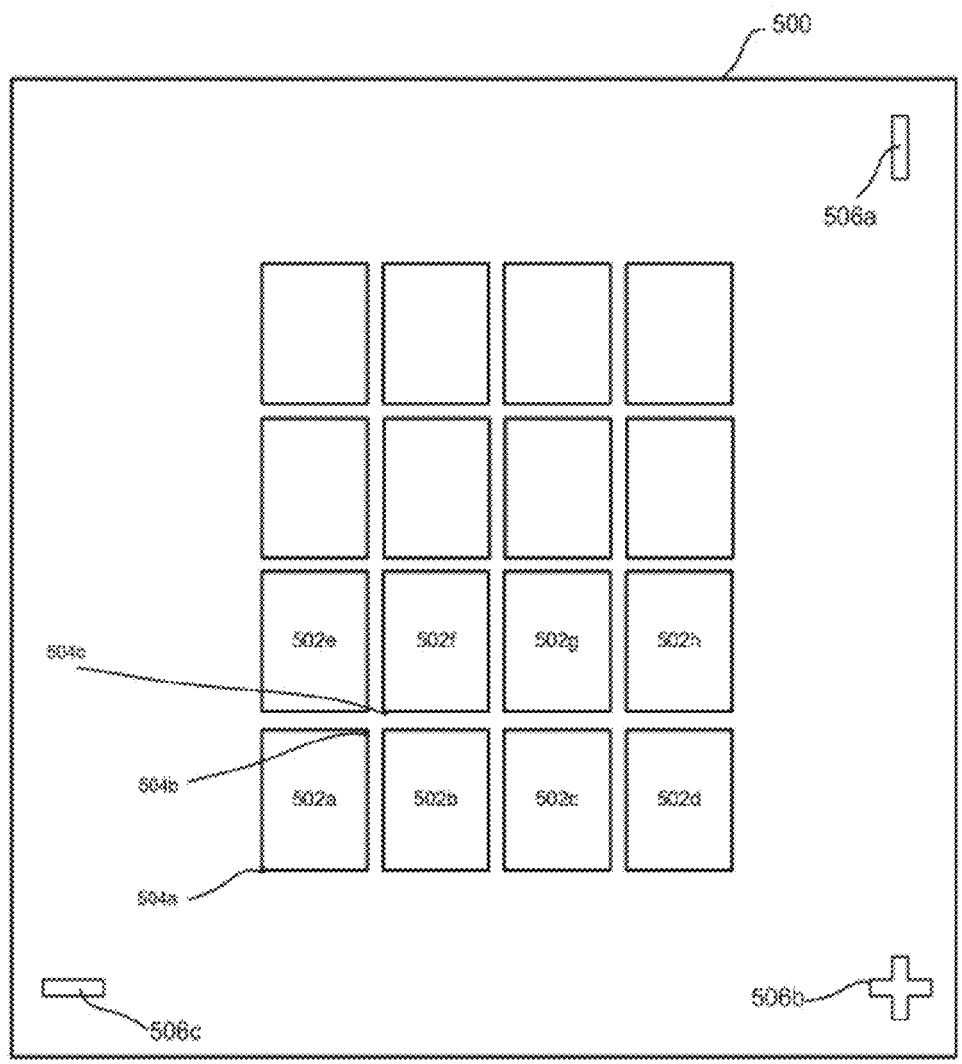
FIG. 5 illustrates a reticle having an array of dies for which an extent, offset, and array size are defined during a setup procedure in accordance with one example implementation of the present invention.

FIG. 4 is a flow chart illustrating a procedure for swath management in accordance with one embodiment of the present invention. The positions of $1^{st}$ and $2^{nd}$ opposite edges of each identical die of a reticle may be initially defined in operation 402. In general, the inspection tool may be set up with information regarding each die's extent, die offsets, and an array size. FIG. 5 illustrates a reticle 500 having an array of dies (e.g., 502a~h) for which an extent, offset, and array size are defined with respect to an inspection tool in accordance with one example implementation of the present invention. In a specific implementation, a setup process for an inspection tool may first include a mechanism for aligning a reticle in the tool. The reticle may be positioned by a user with respect to any suitable number and type of alignment marks, such as 506a~c, on the reticle so as to align the reticle and define a particular coordinate system for the reticle scan.

Through a setup process for the inspection tool, a user may select points 504a and 504b to define the extent of a first die 502a, as well as the extent of all other dies, if all the dies are identical. The user may also select point 504c to define an x and y offset with respect to die 502a and all other dies if their offsets from each other are the same. Other points (not shown) may also be selected to define extents and offsets. The array size may be input by the user into the inspection tool.

Figure 3D:
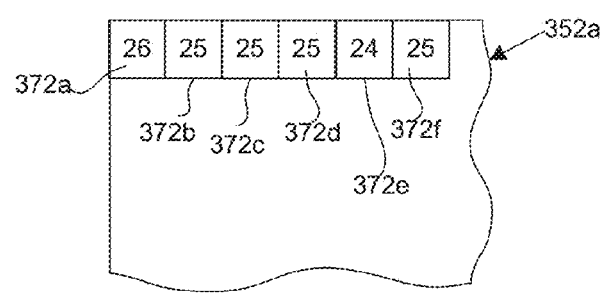
FIG. 3D is a diagrammatic illustration of multiple intensity data sets that corresponds to multiple local areas of a patch of a swath of the reticle in accordance with an example implementation.

The inspection tool may use the defined die extent, die offsets, and array size to automatically define each die's position and determine how to position the swath scans. Referring back to FIG. 4, a $1^{st}$ swath's relative position with respect to the first edge of a $1^{st}$ set of dies may be defined so that the $1^{st}$ swath includes the $1^{st}$ edges of the $1^{st}$ set or row of dies in operation 403. In the example of FIG. 3D, the $1^{st}$ swath 304a is defined relative to the bottom edges (e.g., 306a~306c) of the $1^{st}$ set of dies (e.g., 302a~302c). The $1^{st}$ swath may also be defined relative to any other equivalent positions of the $1^{st}$ set of dies. A swath may generally be defined with respect to a particular die position by the inspection tool automatically initiating a scan at a particular swath position.

The beam of the inspection tool may then be scanned across the $1^{st}$ swath of the reticle so as to obtain images of the $1^{st}$ swath in operation 404. In one example, an optical beam may scan across the reticle and intensity values may be collected for each pixel or point of the $1^{st}$ swath as such beam scans across such $1^{st}$ swath. Said in another way, the inspection tool may be operable to detect and collect reflected and/or transmitted light as an incident optical beam scans across the $1^{st}$ swath. Light is collected in response to this incident beam from a plurality of points or subareas of the $1^{st}$ swath.

In the example of FIG. 3D, $1^{st}$ swath 304a includes a $1^{st}$ edge 306a of die 302a, a $1^{st}$ edge 306b of die 302b, and a $1^{st}$ edge 306c of die 302c. Each die also has a $2^{nd}$ opposite edge (e.g., 308a, 308b, and 380c). After the $1^{st}$ swath is scanned, it may then be determined whether a next adjacent swath would include the 1$^{st}$ edges of a next set or row of dies in operation 406. If the 1$^{st}$ edges of a next set of dies have not yet been reached, the next swath's position may be defined to be adjacent or overlapping with the previously scanned swath in operation 410. The swaths will tend to be overlapping so as to facilitate alignment of die images as further described below. The beam may also be scanned across this defined next swath so as to obtain images of the next swath in operation 412. It may then be determined whether all the dies have been scanned in operation 414. If not, the next swaths continue to be defined and scanned until all the dies are scanned and the reticle scan is complete.

The next adjacent swath that is defined and scanned after the 1$^{st}$ swath 304a in FIG. 3D is swath 304b, which has not reached the 1$^{st}$ edges 306d~306e of the 2$^{nd}$ set of dies 302d~302f. In this illustration, the next swath 304b is positioned adjacent to the 1$^{st}$ swath 304a. Swaths 304c~304f are sequentially defined and scanned as next swaths, which are each positioned adjacent to or overlapping with the previously scanned swath, and these next swaths are sequentially scanned with the inspection tool's optical beam to obtain patch images.

The adjacent swaths could continue to be scanned after swath 304g is scanned (e.g., 304h~304l) as in the first implementation of FIG. 3A. For instance, swath 304g~304l are scanned so as to form adjacent or overlapping swaths 304a~304l. However, the scanned swaths of the 2$^{nd}$ set of dies (e.g., 302d~302f) would not be positioned in same way relative to the die edges as the swaths of the 1$^{st}$ set of dies (e.g., 302a~302c). For example, the images of swath 304g are not aligned to the 1$^{st}$ edges of the 2$^{nd}$ set of dies 302d~f in the same way that the patch images of the 1$^{st}$ swath 304a are aligned to the 1$^{st}$ edges of the 1$^{st}$ set of dies 302a~c. In this embodiment, the swaths would be scanned so as to overlap enough so that portions of the swaths for different die rows may be selectively analyzed to form die-equivalent patches.

The illustrated optional second implementation includes repositioning of the next scan when a new set of dies are to be scanned. If the 1$^{st}$ edges of the next set of dies will be reached in the next scan, the next swath's relative position may be set with respect to the first edges of the next set of the dies to be identical to the 1$^{st}$ swath's relative position with respect to the 1$^{st}$ set of dies in operation 408. After swath 304f is scanned, the next swath to be scanned is defined as swath 392a in the example of FIG. 3D, which aligns to the first edges 306d~f of the second set of dies 302d~f. The beam is then scanned across this next swath so as to obtain images in operation 412. The procedure 400 repeats until the last swath is scanned.

After images are obtained for all the dies (or optionally only two or more dies), each die image may be aligned with respect to another die image prior to performing an inspection process. For instance, each test die image can be aligned with a corresponding reference die image. In one example illustrated in FIG. 5, the image of test die 502a may be aligned with the image reference die 502b; while the image of test die 502b is aligned with the image of reference die 502c; etc. This alignment technique may result in false defects caused by the different paired die alignments. That is, since all dies are not aligned in the same way, there may be discrepancies between the patterns in each die-equivalent image patch so that edge patterns for different pairs of test and reference patches are not the same.

In an alternative embodiment illustrated in FIG. 2, each die image may be aligned with a single "golden die" in operation 203. For instance, each die of FIG. 5 may be aligned with golden die 502a so that a same alignment is provided. That is, dies 502b, 502c, 502d, 502e, etc. are aligned with die 502a. Any other die may be selected as the golden die to which the other dies are aligned. Alignment may include overlaying each die's image to the golden die image and incrementally moving the overlaid die (e.g., by ±5 pixels) until there is a maximum fit (or minimal difference) between the two die images.

An alignment process may involve selecting portions of each swath from overlapping swaths, which were collected from the inspection tool, for use in the inspection analysis. Since there is typically an overlap in both x and y directions between swaths, outer swath portions may be discarded so that the remaining swaths align with each other and are the same in each die. For instance, after aligning each die image to the golden die image and retaining certain swath portions from each die, each die image includes swaths and patches having positions that correspond to the aligned golden die swath and patches positions (e.g., with respect to a reference mark). One or more swaths may also be kept for the gap between die rows if needed so as to not have an uninspected reticle area (which may include test targets in the scribe line). The second implementation for managing swath scanning as described above would result in less discarding of swath portions and corresponding patches for dies that were not in the same row as the golden die.

Referring back to FIG. 2, an integrated value for an image characteristic, such as an integrated intensity value, may be determined for each patch (or multiple patches) in operation 204. FIG. 3D is a diagrammatic illustration of multiple intensity data sets that corresponds to multiple local areas (e.g., 372a~372f) of a patch of a swath of the reticle. In certain implementations, an average or median reflected and/or transmitted intensity value may be determined for each patch or set of two or more patches. As shown, multiple intensity values (e.g., 372a, 372b, 372c, 372d, 372e, and 372f) correspond to multiple pixels or points of a particular patch 352a of a particular swath of a reticle. For example, intensity data set corresponding to patch 352a of the reticle may include intensity values 26, 25, 25, 25, 24, 25, etc. All of the intensity values for the patch may be averaged together to determine an average intensity value (e.g., 25) for such patch.

The intensity values corresponding to the reflected light may also be combined with the intensity values for the transmitted light before or after determining the average reflected and transmitted intensity value for each patch. For instance, an average of the reflected and transmitted intensity values may be determined for the points or pixels of each patch. Alternatively, the averages may be calculated separately for the reflected and transmitted intensity values of a patch. The separately calculated reflected average and transmitted average for each patch may also be combined or averaged together.

In an alternative embodiment, the integrated intensity value for each patch may be generated based on reflected light, transmitted light, or both as detected during reticle inspections. In one example implementation, the reflected (R) and transmitted (T) values may be combined by (T−R)/2. The reflected signal typically is the opposite sign from the transmitted signal. Hence, subtracting the T and R signals adds the signals together. Since the noise sources are different for T and R, the noise can tend to be averaged out of the combined signal. Other weightings to R and/or T values may be used to generate integrated intensity values for a patch with associated benefits. In some cases, R and T signals for particular regions may have a same sign, instead of an opposite sign, which may indicate that the results are inconsistent in the associated regions and may not be trustworthy. Thus, the combination of R and T could be down-weighted in such regions or removed from the computation if insufficiently trustworthy.

Figure 6A:
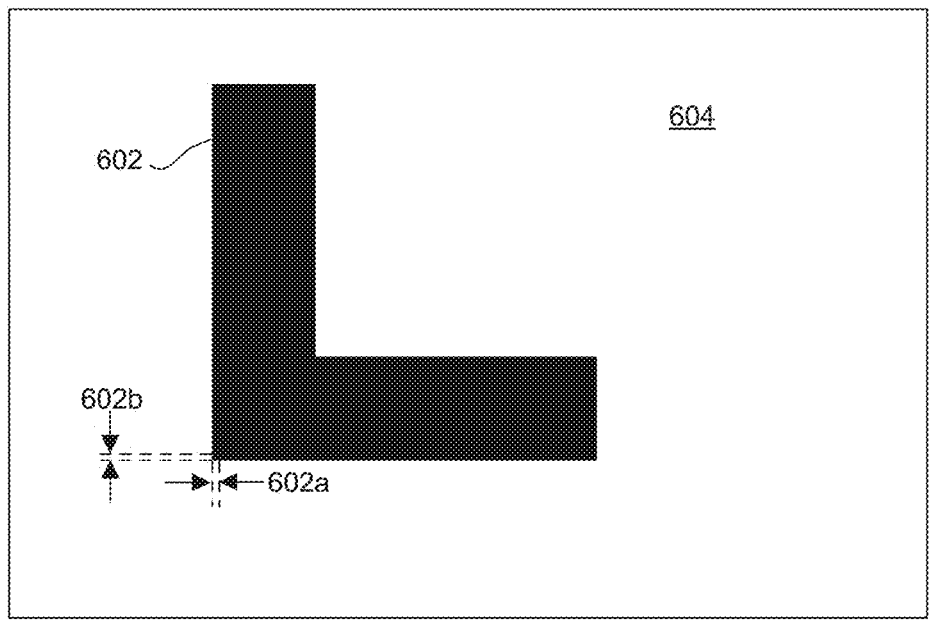
FIG. 6A is a diagrammatic of a patch area having a dark structure surrounded by a light background area.

Various techniques may be employed for compensating for the effects of variable pattern sparseness of different patches on the resulting integrated intensity values for such patches. Said in another way, a pattern sparseness metric may be used to gain up or down the integrated intensity value of each patch based on such patch's relative pattern sparseness metric relative to other patches' pattern sparseness metric. In the illustrated embodiment, a local number of edge pixels may be determined for each patch in operation 204. An average number of edge pixels may also be determined for the patches of the reticles in operation 208. The number of edge pixels for a particular patch may be determined in any suitable manner. For instance, the pixels that are part of an area having a particular intensity and also adjacent to other pixels that have a significantly different intensity may be defined as edge pixels. FIG. 6A is a diagrammatic of a patch area having a dark structure 602 surrounded by a light background area 604. The dark pixels along the borders of the dark structures, such as borders 602a and 602b, can be easily defined as edge pixels since the contrast is high between these structure pixels and the adjacent pixels of the surrounding field 604. That is, the sharp roll-off between light and dark on a patch image only spans single border pixels.

Figure 6B:
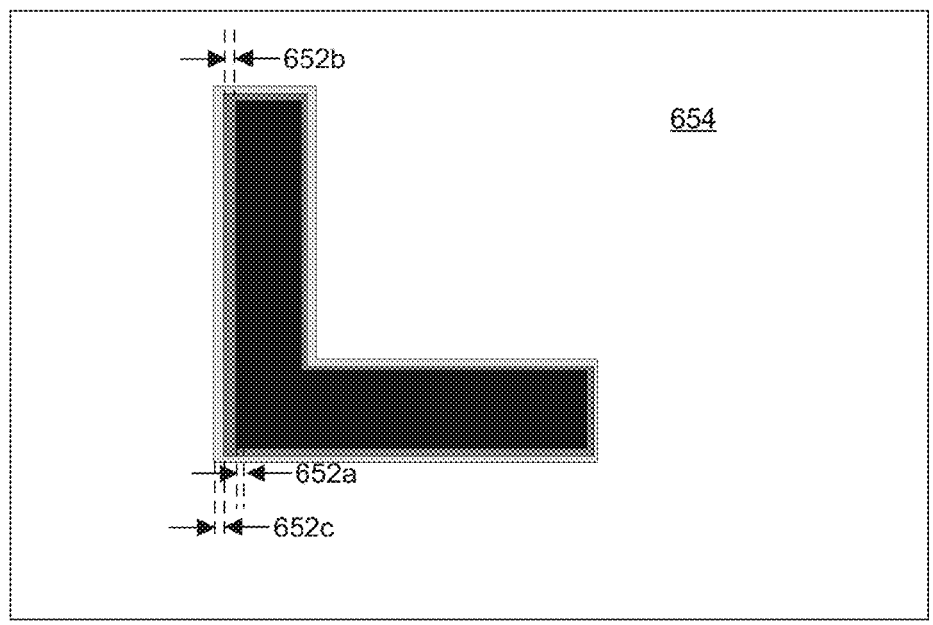
FIG. 6B is a diagrammatic of a patch area having a dark structure surrounded by a light background area having a more gradual intensity change at its border than the patch of FIG. 6A.

In most images of reticle structures, there may not be a sharp roll-off of the intensity along a structure's border. FIG. 6B is a diagrammatic of a patch area having a dark structure surrounded by a light background area 654 having a more gradual intensity change at its border. As shown, the structure includes a dark inner border portion 652a, a medium gray border portion 652b, and a lighter gray border portion 652c although the border region may typically have even more shades of grey. Thus, more pixels in the border regions (652a~c) are involved with the intensity roll-off from dark to light and may be defined as edge pixels.

A higher edge pixel count for gradual intensity changes of the structure borders in particular patches may adversely affect the quantification of the pattern sparseness for such patches, as compared to patches with steeper edge roll-offs. Thus, a buffer of pixels may be selected for including or excluding from the identification of edge pixels to indicate that a pixel edge can be a predefined width, such as 1 or 2 pixels wide. A pixel edge width is generally determined by the optical system and the sampling strategy. For instance, the pixel edge width generally pertains to the maximum extend of the edge impact on the image.

Referring back to FIG. 2, a gain may be applied to each patch intensity value in operation 210. The gain for each patch may be based on the ratio between the average edge pixel count and such patch's local edge pixels count. For example, patches that have sparse patterns with lower edge pixel counts, as compared to the average count, would result in a positive gain for the intensity signals, while patches that were more sparse and had higher edge pixels counts than the average count would result in a negative gain or a decrease for the intensity value for such patches.

The amount of gain to apply to each patch's intensity signal may be limited by a predefined amount. This approach may be useful to prevent a divide-by-zero problem or prevent using so much gain that the gained-up noise would be a problem. Examples of gain limits include a threshold for absolute gain up/down or by the following equation: (patch signal)*(average edge pixel count)/Max (patch edge pixel count, 1000). This equation would limit the denominator to some minimum value, such as 1000. Other minimum values may be used.

A difference between an intensity value of each test patch of each die and a reference value of a corresponding reference patch may then be determined in operation 212. A delta-intensity map may then be generated based on the determined intensity differences in operation 214. Embodiments of a delta-intensity map can take any suitable form. For example, a delta-intensity map can be represented textually as a list of average intensity variation values for each area of the reticle. Each average intensity variation value may be listed alongside corresponding reticle area coordinates. A delta-intensity map can also be represented by a metric such as the standard deviation or variance of the grid point difference values. Alternatively or additionally, an intensity variation map may be represented visually so that different intensity variation values or ranges are shown as different visual ways, such as differently colored reticle areas, different bar graph heights, different graph values, or 3-dimensional representations, etc. An intensity map can be represented with different grid point sampling sizes or by fits to different functional forms such as a polynominal fit or a Fourier transform.

While the delta-intensity (or $\Delta I$) map may be used to track problem areas on the reticles, for example, that are caused by reticle fabrication issues or degradation of a reticle over time, such as chrome, MoSi, pellicle, cleaning type degradations, it would be beneficial to also track more specific metrics of changes across the reticle, such as $\Delta CD$. In certain embodiments of the present invention, a calibration process includes the use of patterns that were used to fabricate or exists in the region of interest to calculate a conversion factor from a change in intensity to a change in CD. A calibration between known $\Delta CD$ and expected $\Delta I$ can be set up, stored, and then used to convert a $\Delta I$ map to a $\Delta CD$ map.

Figure 7:
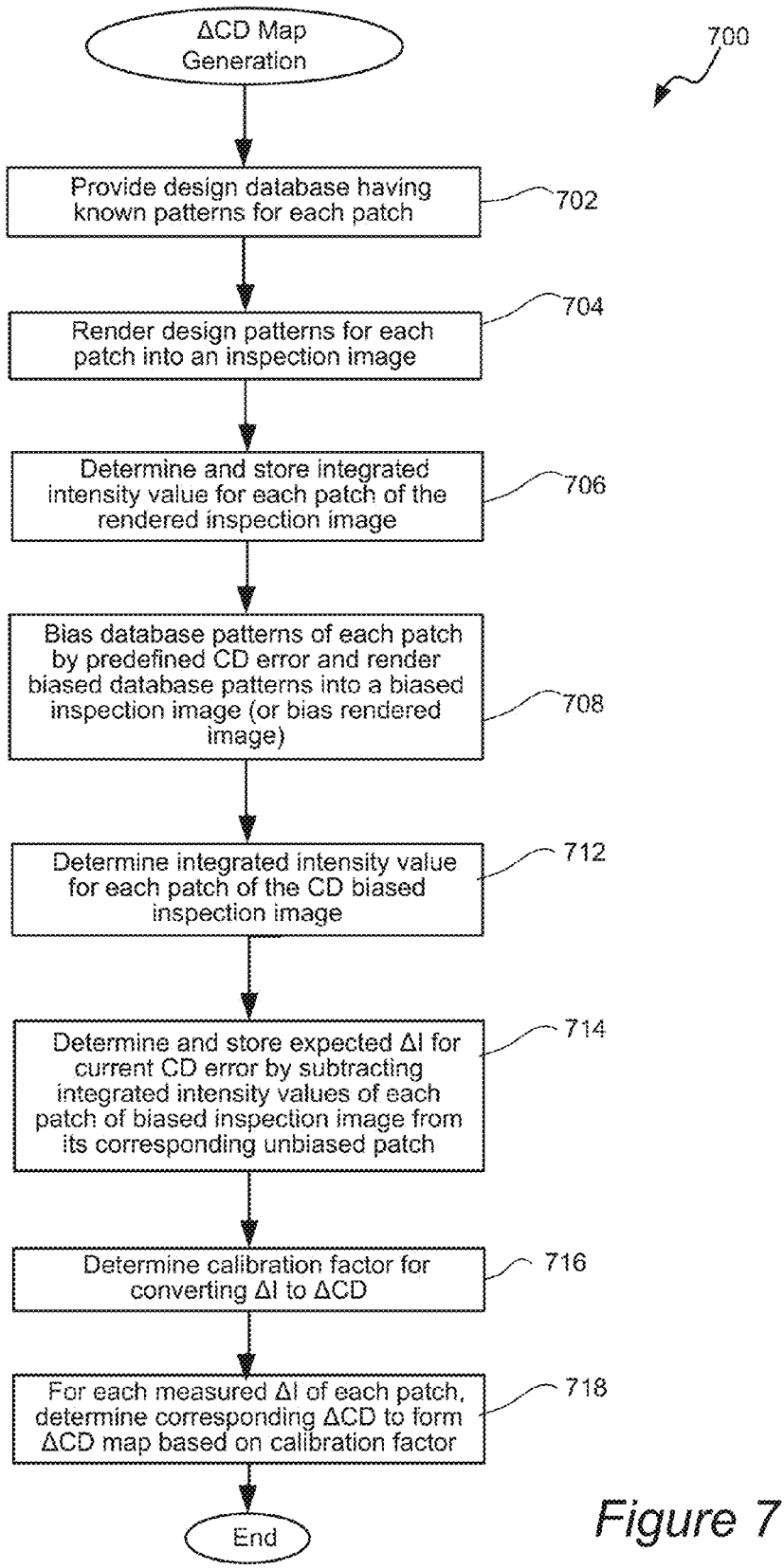
FIG. 7 is a flow chart illustrating a procedure for generating a critical dimension map in accordance with a specific implementation of the present invention.

FIG. 7 is a flow chart illustrating a procedure 700 for generating a delta-CD map in accordance with one embodiment of the present invention. In this embodiment, the design database having known patterns for each patch is first provided in operation 702. The design database would typically be available in a die-to-database defect inspection, for example, immediately after the reticle is fabricated. Although the design database is preferable retained by the reticle manufacturer, the design database may also be made available for inspection in the wafer fabrication facility, e.g., for inspecting the reticle after use of the reticle to fabricate devices.

In the illustrated embodiment, the design patterns for each patch may be rendered into an inspection image in operation 704. For example, each rendered inspected image may include reflected and transmitted values, which would be obtained from optically inspecting the corresponding patch of a reticle that is fabricated with such design pattern. The rendered inspected image may be obtained using any tool, such as Teron630 available from KLA-Tencor Corp. of Milpitas, Calif. An integrated intensity value for each patch of the rendered inspection image may then be determined and stored in operation 706. For instance, the rendered reflected and transmitted intensity values may be averaged together for each rendered patch (e.g., to obtain an average reflected value and an average transmitted value or an averaged combined reflected and transmitted value).

The database patterns for each patch may then be biased by a predefined CD error in operation 708. For instance, the database patterns for each patch are all biased by a known CD error value of 5 nm. This bias operation can be performed on the database figures themselves, or it can be performed after a rasterization or rendering operation on the rendered image. This biased image is now rendered to match the intensity that would be seen by the inspection station. The integrated intensity value computation may then be determined for each patch of the CD biased inspection image in operation 712.

The expected ΔI for the CD bias may then be determined and stored by subtracting the integrated intensity value for each patch of the CD biased inspection image from its corresponding unbiased patch in operation 714. A calibration factor for converting ΔI to ΔCD for each patch may then be determined in operation 716. The calibration factor for each patch may be provided by the slope of ΔCD by the resulting ΔI for such rendered patch. For each ΔI of each inspected patch, a corresponding ΔCD may be determined to form a ΔCD map in operation 718. The calibration factor can be applied to the measured ΔI signal that is not gained up or down based on sparseness levels of the patches since the ΔI from the rendered database image upon which the calibration factor was based will have matching sparseness effects.

The calibration factor for each patch may also be stored and used in monitoring CD uniformity after the reticle is used for a predetermined time period or number of fabrication processes. That is, the above-described inspection procedures, such as the procedures of FIGS. 2 and 7, are repeated for the used reticle after photolithography processes have been repeatedly implemented with the reticle.

The slope is only part of the calculation for the calibration factor for each patch. To get the CD offset value (or average CD on the mask relative to the average intended design CD) is a separate measure that requires very accurate rendering of the image. Although this is theoretically possible and a straightforward result of database rendering, it is typically limited by rendering quality and the noise of the imaging process. It is also possible to determine the absolute CD based on the measured intensity signals.

Certain embodiment of the present invention can provide compensation for pattern density effects in the formation of the CDU map, while reducing noise. Calibration embodiments also can have the additional advantage of converting the map from a delta-intensity measure to a delta-CD measure.

Additionally, other types of problems that may affect yield, besides CD uniformity errors, can be found with the above described techniques. For instance, certain types of defects may result in local transmissivity errors that can be yield limiting. One type of defect that causes local transmissivity issues is a glass-side water spot that can affect the functionality of the printed wafer.

Note also that it is possible to perform the above described operation without the use of the design database. In this case the original image from a known good reticle may be used for the reference value, and a CD bias may then be imposed directly onto this original image to get the CD-biased image. A new reticle that is verified as free of degradation and defects, for example, may be used as a known good reticle. The direct biasing of the optical image may be accomplished by a "mask pattern recovery" step, as described further in U.S. Pat. No. 8,855,400 issued 7 Oct. 2014 by Wang et al., which is incorporated herein by reference in its entirety. In this manner, the images from both transmitted and reflected light can be used to get an equivalent mask image which can then be more readily biased.

In general, the CD value depends on the pattern edges, especially how the edge locations affect the transmission signal. That is, the pattern edges are what is important for monitoring CD uniformity. However, there is noise that comes from both the edge regions and from the flat-field regions. In sparse patterns, there are fewer edges and, hence, any measured signal is weaker, which means that the noise is more important in those sparse regions because any approach to gain-up that weak signal could be gaining up noise as well. Since there is no useful signal coming from the flat field areas for a CD uniformity application, it makes sense to eliminate the noise from these areas.

In one embodiment, a flat field region is defined as a region that is located a particular distance from a pattern edge, and the measured image value (which contains noise) from this flat field region is replaced with a corresponding constant, such as the nominal light calibration value for that region. For instance, a line structure image's internal region is defined as black (minimum light calibration value), while the region surrounding the line structure image is defined as white (maximum light calibration value). This way, all the noise in the flat field regions is eliminated, and only the edge noise remains. The use of a constant in all test and reference regions should perfectly cancel.

This technique for managing noise in flat field regions will avoid image noise from these flat field regions from degrading the signal that is important for measuring CD changes. Any suitable distance from edge regions may be used to define the flat field regions. In other words, any suitable edge buffer may be used so that constant intensity values are assigned to regions outside the edge buffer. In one example, the region where the pattern edge no longer has significant influence on the measured light value for any of the test or reference dice can be defined as a flat field region. In a specific example, the edge regions are defined as being ±5 pixels wide, depending on the pixel size and the desired optimization of noise minimization. The image is nominally unvarying, except for noise in this region. Note that it is helpful to have good alignment between all of the corresponding patches to ensure that the edge definition is the same for each of those patches as described further above.

Additionally, this technique for defining flat field regions may be used in a die-to-database inspection, in which the reference die is obtained from an image that is rendered from the design database. This technique may be more important in die-to-die inspection since noise is likely present in both the test and reference dies, while a die-to-database inspection only has noise from the test die and not the reference die.

A global intensity offset may be used to determine a global CD variation. That is, a global CD variation may be associated with a ΔI map's global intensity offset. Both the transmitted and reflected light signal may be analyzed to compensate for noise while determining a global CD change. The parts of the R and T maps that "agree" can be used for determining a CD offset, while the parts of those that "disagree" imply noise of some type (i.e., birefringence, reflectivity changes) and are not used for determining a CD offset. It is also preferable that the inspection light levels are properly calibrated and compensated.

One way to determine a global offset is to compute the full mask mean for the inspection. This full mask mean can then be subtracted from the ΔI map results. However, for relatively noise-free results, the global offset can be very meaningful, for example, even if there was no apparent spatial distribution change. This global offset can represent the global CD change.

After a ΔI or ΔCD map is generated, one or both of the maps may be analyzed. For instance, it may be determined whether any variation in average ΔI or ΔCD for a same reticle area is above a predefined threshold. If an average ΔI or ΔCD is above the predefined threshold, the corresponding reticle portion may then be more carefully reviewed to determine whether the reticle is defective and can no longer be used. For instance, a SEM may be used to review the defective area to determine whether critical dimensions (CD's) are out of specification.

In alternative implementations, specific intensity changes can be associated with specific CD values, which can then be determined to be in or out of specification. In another example implementation, particular intensity changes may be associated with specific CD values through calibration reticles having multiple known CD values that can be measured to determine intensity differences between different CD changes. Although these CD and intensity change correlations are obtained from different areas of the calibration reticle, these associations may be applied to each intensity difference for each same reticle area to determine CD variation for such same reticle area.

An out-of-specification CD would result in the reticle not passing the inspection. If the reticle fails inspection, the reticle may be discarded or repaired if possible. For instance, certain defects can be cleaned from the reticle. After repair, a new reference inspection may be performed on the cleaned reticle and the procedure repeated.

Figure 8:
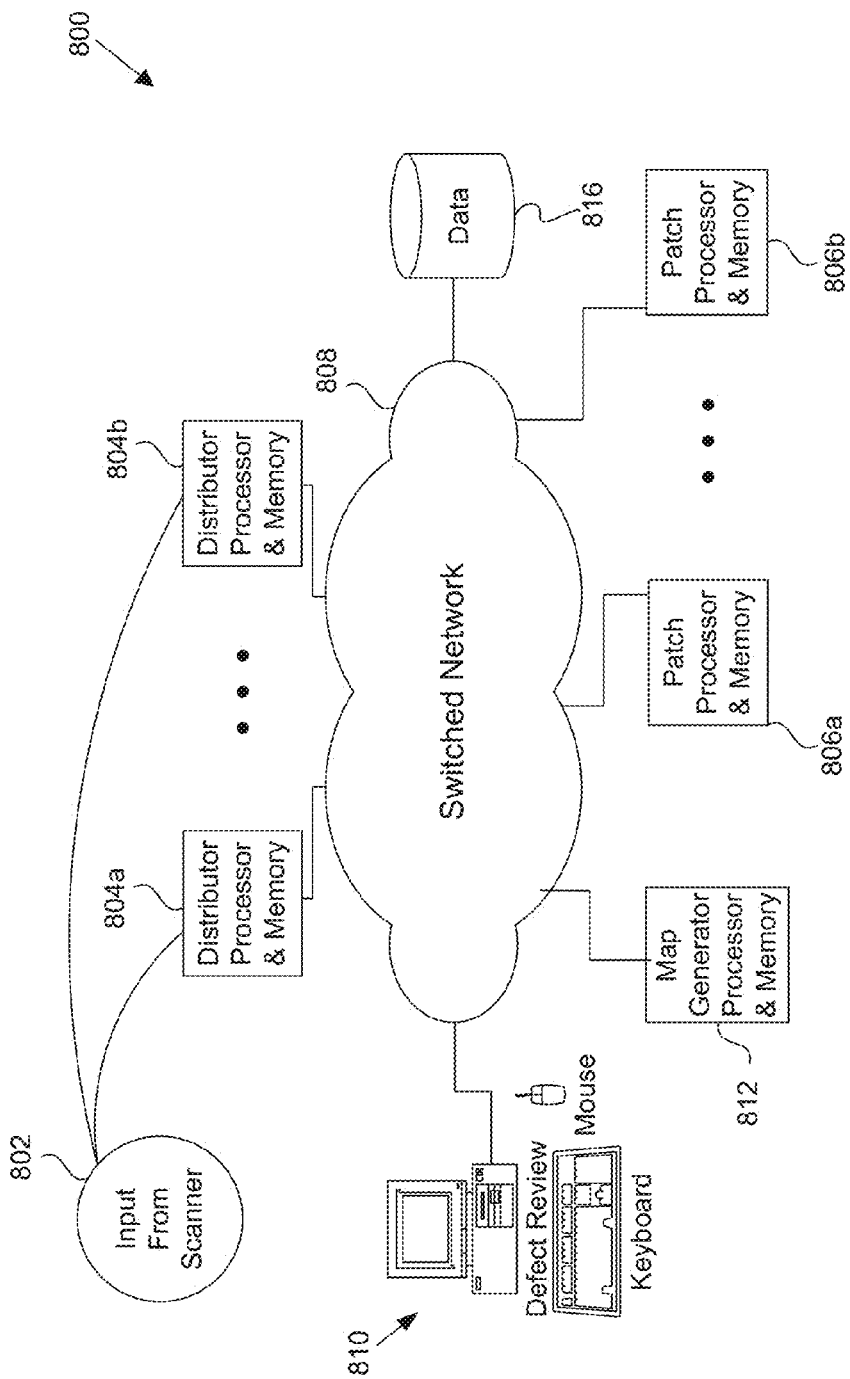
FIG. 8 is a diagrammatic representation of an example inspection system in which techniques of the present invention may be implemented

Techniques of the present invention may be implemented in any suitable combination of hardware and/or software. FIG. 8 is a diagrammatic representation of an example inspection system 800 in which techniques of the present invention may be implemented. The inspection system 800 may receive input 802 from an inspection tool or scanner (not shown). The inspection system may also include a data distribution system (e.g., 804*a* and 804*b*) for distributing the received input 802, an intensity signal (or patch) processing system (e.g., patch processors and memory 806*a* and 806*b*) for processing specific portions/patches of received input 802, a map generator system (e.g., Map Generator Processor and Memory 812) for generating a ΔI and ΔCD maps, a network (e.g., switched network 808) for allowing communication between the inspection system components, an optional mass storage device 816, and one or more inspection control and/or review stations (e.g., 810) for reviewing the maps. Each processor of the inspection system 800 typically may include one or more microprocessor integrated circuits and may also contain interface and/or memory integrated circuits and may additionally be coupled to one or more shared and/or global memory devices.

The scanner or data acquisition system (not shown) for generating input data 802 may take the form of any suitable instrument (e.g., as described further herein) for obtaining intensity signals or images of a reticle. For example, the scanner may construct an optical image or generate intensity values of a portion of the reticle based on a portion of detected light that is reflected, transmitted, or otherwise directed to one or more light sensors. The scanner may then output the intensity values or image may be output from the scanner.

The reticle is generally divided into a plurality of patch portions from which multiple intensity values from multiple points are obtained. The patch portions of the reticle can be scanned to obtain this intensity data. The patch portions may be any size and shape, depending on the particular system and application requirements. In general, multiple intensity values for each patch portion may be obtained by scanning the reticle in any suitable manner. By way of example, multiple intensity values for each patch portion may be obtained by raster scanning the reticle. Alternatively, the images may be obtained by scanning the reticle with any suitable pattern, such as a circular or spiral pattern. Of course, the sensors may have to be arranged differently (e.g., in a circular pattern) and/or the reticle may be moved differently (e.g., rotated) during scanning in order to scan a circular or spiral shape from the reticle.

In the example illustrated below, as the reticle moves past the sensors, light is detected from a rectangular region (herein referred to as a "swath") of the reticle and such detected light is converted into multiple intensity values at multiple points in each patch. In this embodiment, the sensors of the scanner are arranged in a rectangular pattern to receive light that is reflected and/or transmitted from the reticle and generate therefrom a set of intensity data that corresponds to a swath of patches of the reticle. In a specific example, each swath can be about 1 million pixels wide and about 1000 to 2000 pixels high, while each patch can be about 2000 pixels wide and 1000 pixels high.

Intensity values for each patch may be obtained using an optical inspection tool that is set up in any suitable manner. The optical tool is generally set up with a set of operating parameters or a "recipe" that is substantially the same for the different inspection runs for obtaining intensity values. Recipe settings may include one or more of the following settings: a setting for scanning the reticle in a particular pattern, pixel size, a setting for grouping adjacent signals from single signals, a focus setting, an illumination or detection aperture setting, an incident beam angle and wavelength setting, a detector setting, a setting for the amount of reflected or transmitted light, aerial modeling parameters, etc.

Intensity or image data 802 can be received by data distribution system via network 808. The data distribution system may be associated with one or more memory devices, such as RAM buffers, for holding at least a portion of the received data 802. Preferably, the total memory is large enough to hold an entire swatch of data. For example, one gigabyte of memory works well for a swatch that is 1 million by 1000 pixels or points.

The data distribution system (e.g., 804*a* and 804*b*) may also control distribution of portions of the received input data 802 to the processors (e.g. 806*a* and 806*b*). For example, data distribution system may route data for a first patch to a first patch processor 806*a*, and may route data for a second patch to patch processor 806*b*. Multiple sets of data for multiple patches may also be routed to each patch processor.

The patch processors may receive intensity values or an image that corresponds to at least a portion or patch of the reticle. The patch processors may each also be coupled to or integrated with one or more memory devices (not shown), such as DRAM devices that provide local memory functions, such as holding the received data portion. Preferably, the memory is large enough to hold data that corresponds to a patch of the reticle. For example, eight megabytes of memory works well for intensity values or an image corresponding to a patch that is 512 by 1024 pixels. The patch processors may also share memory.

Each set of input data 802 may correspond to a swath of the reticle. One or more sets of data may be stored in memory of the data distribution system. This memory may be controlled by one or more processors within the data distribution system, and the memory may be divided into a plurality of partitions. For example, the data distribution system may receive data corresponding to a portion of a swath into a first memory partition (not shown), and the data distribution system may receive another data corresponding to another swath into a second memory partition (not shown). Preferably, each of the memory partitions of the data distribution system only holds the portions of the data that are to be routed to a processor associated with such memory partition. For example, the first memory partition of the data distribution system may hold and route first data to patch processor 806a, and the second memory partition may hold and route second data to patch processor 806b.

The detected signals may also take the form of aerial images. That is, an aerial imaging technique may be used to simulate the optical effects of the photolithography system so as to produce an aerial image of the photoresist pattern that is exposed on the wafer. In general, the optics of the photolithography tool are emulated so as to produce an aerial image based on the detected signals from the reticle. The aerial image corresponds to the pattern produced from the light passed through the photolithography optics and reticle onto the photoresist layer of a wafer. Additionally, the photoresist exposure process for the particular type of photoresist material may also be emulated.

The incident light or detected light may be passed through any suitable spatial aperture to produce any incident or detected light profile at any suitable incident angles. By way of examples, programmable illumination or detection apertures may be utilized to produce a particular beam profile, such as dipole, quadrapole, quasar, annulus, etc. In a specific example, Source Mask Optimization (SMO) or any pixelated illumination technique may be implemented.

The data distribution system may define and distribute each set of data of the data based on any suitable parameters of the data. For example, the data may be defined and distributed based on the corresponding position of the patch on the reticle. In one embodiment, each swath is associated with a range of column positions that correspond to horizontal positions of pixels within the swath. For example, columns 0 through 256 of the swath may correspond to a first patch, and the pixels within these columns will comprise the first image or set of intensity values, which is routed to one or more patch processors. Likewise, columns 257 through 512 of the swath may correspond to a second patch, and the pixels in these columns will comprise the second image or set of intensity values, which is routed to different patch processor(s).

Figure 9A:
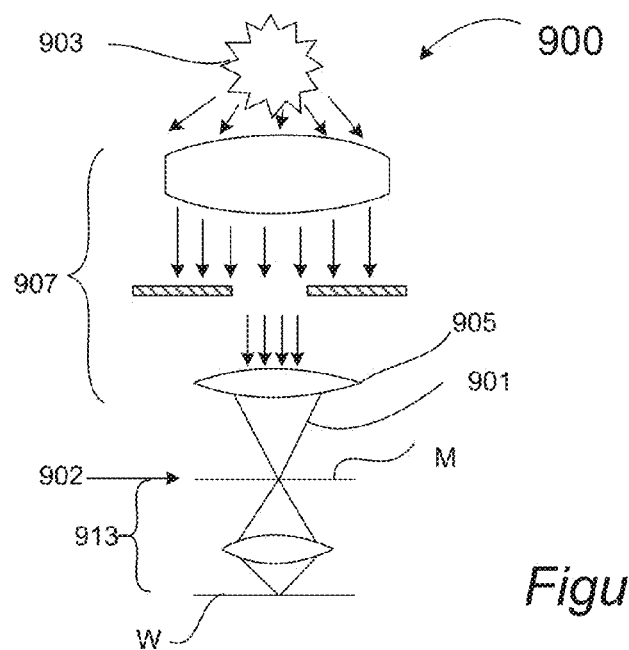
FIG. 9A is a simplified schematic representation of a lithographic system for transferring a mask pattern from a photomask onto a wafer in accordance with certain embodiments.

FIG. 9A is a simplified schematic representation of a typical lithographic system 900 that can be used to transfer a mask pattern from a photomask M onto a wafer W in accordance with certain embodiments. Examples of such systems include scanners and steppers, more specifically PAS 5500 system available from ASML in Veldhoven, Netherlands. In general, an illumination source 903 directs a light beam through an illumination optics 901 (e.g., lens 905) onto a photomask M located in a mask plane 902. The illumination lens 905 has a numeric aperture 901 at that plane 902. The value of the numerical aperture 901 impacts which defects on the photomask are lithographic significant defects and which ones are not. A portion of the beam that passes through the photomask M forms a patterned optical signal that is directed through imaging optics 913 and onto a wafer W to initiate the pattern transfer.

Figure 9B:
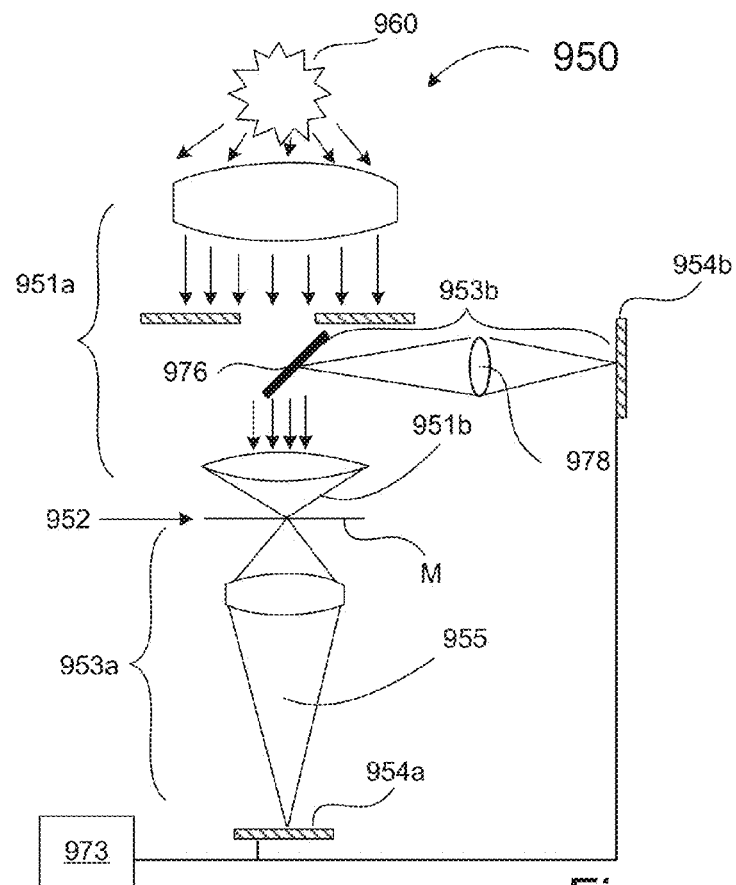
FIG. 9B provides a schematic representation of a photomask inspection apparatus in accordance with certain embodiments.

FIG. 9B provides a schematic representation of an example inspection system 950 that has illumination optics 951a includes an imaging lens with a relative large numerical aperture 951b at a reticle plane 952 in accordance with certain embodiments. The depicted inspection system 950 includes detection optics 953a and 953b, including microscopic magnification optics designed to provide, for example, 60-200× magnification or more for enhanced inspection. For example, the numerical aperture 951b at the reticle plane 952 of the inspection system may be considerable greater than the numerical aperture 901 at the reticle plane 902 of the lithography system 900, which would result in differences between test inspection images and actual printed images.

The inspection techniques described herein may be implemented on various specially configured inspection systems, such as the one schematically illustrated in FIG. 9B. The illustrated system 950 includes an illumination source 960 producing a light beam that is directed through illumination optics 951a onto a photomask M in the reticle plane 952. Examples of light sources include lasers or filtered lamps. In one example, the source is a 193 nm laser. As explained above, the inspection system 950 may have a numerical aperture 951b at the reticle plane 952 that may be greater than a reticle plane numerical aperture (e.g., element 901 in FIG. 9A) of the corresponding lithography system. The photomask M to be inspected is placed on a mask stage at the reticle plane 952 and exposed to the source.

The patterned image from the mask M is directed through a collection of optical elements 953a, which project the patterned image onto a sensor 954a. In a reflecting system, optical elements (e.g., beam splitter 976 and detection lens 978) direct and capture the reflected light onto sensor 954b. Suitable sensors include charged coupled devices (CCD), CCD arrays, time delay integration (TDI) sensors, TDI sensor arrays, photomultiplier tubes (PMT), and other sensors.

The illumination optics column may be moved respect to the mask stage and/or the stage moved relative to a detector or camera by any suitable mechanism so as to scan patches of the reticle. For example, a motor mechanism may be utilized to move the stage. The motor mechanism may be formed from a screw drive and stepper motor, linear drive with feedback position, or band actuator and stepper motor, by way of examples.

The signals captured by each sensor (e.g., 954a and/or 954b) can be processed by a computer system 973 or, more generally, by one or more signal processing devices, which may each include an analog-to-digital converter configured to convert analog signals from each sensor into digital signals for processing. The computer system 973 typically has one or more processors coupled to input/output ports, and one or more memories via appropriate buses or other communication mechanisms.

The computer system 973 may also include one or more input devices (e.g., a keyboard, mouse, joystick) for providing user input, such as changing focus and other inspection recipe parameters. The computer system 973 may also be connected to the stage for controlling, for example, a sample position (e.g., focusing and scanning) and connected to other inspection system components for controlling other inspection parameters and configurations of such inspection system components.

The computer system 973 may be configured (e.g., with programming instructions) to provide a user interface (e.g., a computer screen) for displaying resultant intensity values, images, and other inspection results. The computer system 973 may be configured to analyze intensity changes, phase, and/or other characteristics of reflected and/or transmitted sensed light beam. The computer system 973 may be configured (e.g., with programming instructions) to provide a user interface (e.g., on a computer screen) for displaying resultant intensity values, images, and other inspection characteristics. In certain embodiments, the computer system 973 is configured to carry out inspection techniques detailed above Because such information and program instructions may be implemented on a specially configured computer system, such a system includes program instructions/computer code for performing various operations described herein that can be stored on a computer readable media. Examples of machine-readable media include, but are not limited to, magnetic media such as hard disks, floppy disks, and magnetic tape; optical media such as CD-ROM disks; magneto-optical media such as optical disks; and hardware devices that are specially configured to store and perform program instructions, such as read-only memory devices (ROM) and random access memory (RAM). Examples of program instructions include both machine code, such as produced by a compiler, and files containing higher level code that may be executed by the computer using an interpreter.

In certain embodiments, a system for inspecting a photomask includes at least one memory and at least one processor that are configured to perform techniques described herein. One example of an inspection system includes a specially configured TeraScan™ DUV inspection system available from KLA-Tencor of Milpitas, Calif.

Although the foregoing invention has been described in some detail for purposes of clarity of understanding, it will be apparent that certain changes and modifications may be practiced within the scope of the appended claims. It should be noted that there are many alternative ways of implementing the processes, systems, and apparatus of the present invention. Accordingly, the present embodiments are to be considered as illustrative and not restrictive, and the invention is not to be limited to the details given herein.

What is claimed is:

1. A method of inspecting a photolithographic reticle, the method comprising:
   using an inspection tool to obtain a plurality of patch area images of each patch area of each die of a set of identical dies on a reticle;
   determining an integrated intensity value for each patch area image;
   applying a gain to the integrated intensity value for each patch area image so as to change the integrated intensity value by an amount that is proportional to a pattern sparseness metric that quantifies a pattern density of such patch area image as compared to a pattern density of other patch area images; and
   determining a difference between the integrated intensity value of each patch area image of pairs of the dies, which each pair includes a test die and a reference die, to form a difference intensity map of the reticle, wherein the difference intensity map correlates with a feature characteristic variation that depends on feature edges of the reticle.

2. The method of claim 1, wherein each die's patch area images are aligned with the patch area images of a same one of the dies.

3. The method of claim 1, wherein the integrated intensity value for each patch area image is an average intensity value for a plurality of subareas of the patch area image.

4. The method of claim 1, wherein the sparseness metric of each patch area image of each die is a ratio of an average number of edge pixels of the other patch area images of the die and a local number of edge pixels of such patch area image wherein applying a gain to the integrated intensity value for each patch area image increases the integrated intensity value for each patch area image that has a lower pattern density and corresponding lower number of edge pixels than other patch area images.

5. The method of claim 4, wherein the average and local number of edge pixels are limited to a predefined width of pixels for each feature edge.

6. The method of claim 1, wherein the feature characteristic variation is a critical dimension (CD) variation.

7. The method of claim 6, further comprising using a calibration factor for each patch area of the reticle to convert the difference intensity map to a difference CD map.

8. The method of claim 7, wherein the calibration factor for each patch area is determined from a design database having a known CD value for each patch area that was used to fabricate the reticle.

9. The method of claim 8, wherein the calibration factor for each patch area is determined by:
   rendering an image for each patch area of the reticle based on one or more patterns of the design database corresponding to such patch area;
   for each rendered image for each patch area, determining an expected integrated intensity value;
   by a predefined CD change, either (i) biasing each one or more patterns corresponding to each patch area and rendering the biased one or more patterns into a biased image for such patch area or (ii) biasing one or more patterns of the rendered image for each patch area to form a biased image for such patch area;
   for each biased image for each patch area, determining an expected integrated intensity value;
   for each patch area, determining an integrated intensity difference between the rendered image's integrated intensity value and the biased image's integrated intensity value; and
   for each patch area, determining the calibration factor by dividing the integrated intensity difference by the predefined CD change.

10. The method of claim 8, wherein the calibration factor is stored for each patch area to monitor CD uniformity after using the reticle in one or more photolithography processes.

11. The method of claim 1, further comprising:
   for each patch area image, changing an intensity value to a predefined constant value for any flat field area of the patch area image that is positioned a predefined distance from any feature edge prior to determining the integrated intensity value.

12. The method of claim 11, wherein the predefined distance is selected so that a feature edge does not affect a measured intensity value from an adjacent flat field area.

13. The method of claim 1, wherein the gain that is applied to the integrated intensity value of each patch area image is limited by a predefined amount.

14. An inspection system for inspecting a photolithographic reticle, the system comprising at least one memory and at least one processor that are configured to perform the following operations:
   obtaining a plurality of patch area images of each patch area of each die of a set of identical dies on a reticle;
   determining an integrated intensity value for each patch area image;
   applying a gain to the integrated intensity value for each patch area image so as to change the integrated intensity value by an amount that is proportional to a pattern sparseness metric that quantifies a pattern density of such patch area image as compared to a pattern density of other patch area images; and determining a difference between the integrated intensity value of each patch area image of pairs of the dies, which each pair includes a test die and a reference die, to form a difference intensity map of the reticle, wherein the difference intensity map correlates with a feature characteristic variation that depends on feature edges of the reticle.

15. The system of claim 14, wherein each die's patch area images are aligned with the patch area images of a same one of the dies.

16. The system of claim 14, wherein the integrated intensity value for each patch area image is an average intensity value for a plurality of subareas of the patch area image.

17. The system of claim 14, wherein the sparseness metric of each patch area image of each die is a ratio of an average number of edge pixels of the other patch area images of the die and a local number of edge pixels of such patch area image, wherein applying a gain to the integrated intensity value for each patch area image increases the integrated intensity value for each patch area image that has a lower pattern density and corresponding lower number of edge pixels than other patch area images.

18. The system of claim 17, wherein the average and local number of edge pixels are limited to a predefined width of pixels for each feature edge.

19. The system of claim 14, wherein the feature characteristic variation is a critical dimension (CD) variation.

20. The system of claim 19, wherein the at least one memory and at least one processor are further configured for using a calibration factor for each patch area of the reticle to convert the difference intensity map to a difference CD map.

21. The system of claim 20, wherein the calibration factor for each patch area is determined from a design database having a known CD value for each patch area that was used to fabricate the reticle.

22. The system of claim 21, wherein the calibration factor for each patch area is determined by:
rendering an image for each patch area of the reticle based on one or more patterns of the design database corresponding to such patch area;
for each rendered image for each patch area, determining an expected integrated intensity value;
by a predefined CD change, either (i) biasing each one or more patterns corresponding to each patch area and rendering the biased one or more patterns into a biased image for such patch area or (ii) biasing one or more patterns of the rendered image for each patch area to form a biased image for such patch area;
for each biased image for each patch area, determining an expected integrated intensity value;
for each patch area, determining an integrated intensity difference between the rendered image's integrated intensity value and the biased image's integrated intensity value; and
for each patch area, determining the calibration factor by dividing the integrated intensity difference by the predefined CD change.

23. The system of claim 21, wherein the calibration factor is stored for each patch area to monitor CD uniformity after using the reticle in one or more photolithography processes.

24. The system of claim 14, wherein the at least one memory and at least one processor are further configured for:
for each patch area image, changing an intensity value to a predefined constant value for any flat field area of the patch area image that is positioned a predefined distance from any feature edge prior to determining the integrated intensity value.

25. The system of claim 24, wherein the predefined distance is selected so that a feature edge does not affect a measured intensity value from an adjacent flat field area.

26. The system of claim 14, wherein the gain that is applied to the integrated intensity value of each patch area image is limited by a predefined amount.

27. A non-transitory computer readable medium having instruction stored thereon for performing the following operations:
using an inspection tool to obtain a plurality of patch area images of each patch area of each die of a set of identical dies on a reticle;
determining an integrated intensity value for each patch area image;
applying a gain to the integrated intensity value for each patch area image so as to change the integrated intensity value by an amount that is proportional to a pattern sparseness metric that quantifies a pattern density of such patch area image as compared to a pattern density of other patch area images; and
determining a difference between the integrated intensity value of each patch area image of pairs of the dies, which each pair includes a test die and a reference die, to form a difference intensity map of the reticle, wherein the difference intensity map correlates with a feature characteristic variation that depends on feature edges of the reticle.

* * * * *